United States Patent [19]

Sewell, Jr.

[11] Patent Number: 5,290,276
[45] Date of Patent: Mar. 1, 1994

[54] ROTATABLE LAPAROSCOPIC PUNCTURING INSTRUMENT

[76] Inventor: Frank Sewell, Jr., 1413 N. Elm, Henderson, Ky. 42420

[21] Appl. No.: 832,058

[22] Filed: Feb. 6, 1992

[51] Int. Cl.⁵ .............................................. A61B 17/22
[52] U.S. Cl. ...................... 606/15; 606/185; 604/164
[58] Field of Search ............. 128/4, 6 (U.S. only); 604/164-169; 606/167, 15, 16, 172, 182, 185

[56] References Cited

U.S. PATENT DOCUMENTS

| | | | |
|---|---|---|---|
| 3,856,000 | 12/1974 | Chikama | 128/6 |
| 3,880,148 | 4/1975 | Kanehira et al. | 128/6 |
| 3,941,121 | 3/1976 | Olinger et al. | 128/6 |
| 4,061,135 | 12/1977 | Widran et al. | 128/6 |
| 4,146,019 | 3/1979 | Bass et al. | 128/6 |
| 4,191,191 | 3/1980 | Auburn | 604/164 |
| 4,211,229 | 7/1980 | Wurster | 128/303.1 |
| 4,607,622 | 8/1986 | Fritch et al. | 128/6 |
| 5,169,397 | 12/1992 | Sakashito et al. | 606/185 |

OTHER PUBLICATIONS

Surgical Laparoscopy, K. A. Zucker, 1991, pp. 40-41, 311-322, 340-342.

Laparoscopic Cholecystectomy, J. L. Flowers, et al., Surgical Rounds, Apr. 1991, pp. 271-282.
Advertisement for Auto Sature Disposable FC Kits, Auto Suture Company.

Primary Examiner—Jerome L. Kruter
Attorney, Agent, or Firm—Baker & Daniels

[57] ABSTRACT

An insufflation needle having a viewing system at its distal end and a trocar, both of which can be inserted through rotation of the puncturing element of the instrument, and a method of using these instruments. Both the insufflation needle and the trocar include a rotatable puncturing mechanism and a safety shield which allow the instruments to be safely inserted into body tissue through the use of a drill thereby requiring less force and reducing the possibility of trauma to the patient. The insufflation needle also includes a viewing system which allows the surgeon to view the distal end of the needle while it is being inserted into body tissue as well as to view the distal end of the trocar once it reaches a destination within the abdominal cavity proximate the distal end of the needle. The system reduces the risk of improper placement of both the needle and the trocar to thereby result in a safe laparoscopic surgical procedure.

8 Claims, 6 Drawing Sheets

ROTATABLE LAPAROSCOPIC PUNCTURING INSTRUMENT

FIELD OF THE INVENTION

This invention relates to a surgical instrument and method for laparoscopic surgery, and, in particular, to an instrument having a rotatable puncturing means.

BACKGROUND OF THE INVENTION

Laparoscopic surgery is gaining prominence as the preferred surgical method since the time required for recovery and the risk to the patient are less than with conventional surgical procedures. In laparoscopic surgery, all surgical instruments are inserted through tubes, or trocars, which are placed in small incisions in the abdomen. These small incisions are less susceptible to wound infections and take much less time to heal than the single large incision usually made with conventional techniques. Also, since a large surgical area is not exposed during laparoscopic surgery, the incidence of internal infection is also reduced.

Laparoscopic surgical procedures require that a gas, such as carbon dioxide, be introduced into the abdominal cavity. This establishes pneumoperitoneum wherein the peritoneal cavity is sufficiently inflated for the insertion of trocars into the abdomen. The distal end of the trocars move within the gas-filled cavity and thus provide access to an area larger than the small incision through which the trocar is inserted. During laparoscopic surgery, the flow of gas into the peritoneal cavity continues to replace any gas that is absorbed by the patient or which leaks out through the trocars.

Pneumoperitoneum is established through the use of a special insufflation needle, called a Veress needle, which has a spring-loaded obturator that advances over the sharp tip of the needle as soon as the needle enters the abdominal cavity. This needle is inserted through the fascia and through the peritoneum. Generally, the surgeon relies on tactile senses to determine the proper placement of the needle by recognizing when the needle is inserted through the fascia and then through the peritoneum. However, this technique is often unreliable for a thin patient whose fascia and peritoneum feel like a single layer.

The proper placement of the Veress needle is critical. First, the needle must go through both the fascia and the peritoneum. If the needle is inserted between the fascia and the peritoneum, massive distention of the preperitoneal space therebetween will result. If the needle goes beyond the peritoneum, the needle may perforate the stomach, small bowel, colon, bladder, or major vascular structures, the consequences of which can be fatal. The purpose of the spring-loaded safety tip of the Veress needle is to minimize the risk of visceral injury by covering the sharp tip once it has penetrated the peritoneum. However, in order for the safety tip to be extended, the tip of the needle must reach a void with the tissue. Such a void may not exist for a patient having excessive fat in the abdominal cavity. Thus, it is desirable to utilize a device and a method whereby the insertion of the device can be seen by the surgeon to avoid misplacement of the sharp point of the device.

Present methods for establishing pneumoperitoneum through the use of a Veress needle work very well in normal sized people who have not had previous surgery. They do not work well for those patients who are obese, that have previously had surgery, peritonitis, or severe inflammation. There are also problems in using these methods for patients who have cancer which has spread along the peritoneum. For example, if the patient previously had surgery or has cancer, the intestines may be stuck to the peritoneum with dense fibrous adhesions. In these patients, the needle may go through the peritoneum into the lumen of the bowel.

After establishing pneumoperitoneum, the next step in laparoscopic surgery involves the insertion of a trocar into the abdominal cavity. It is through this first trocar that an endoscope is inserted into the abdominal cavity to provide the surgeon with a view of the rest of the operation. Trocars are similar to the Veress needle in that they are also equipped with a spring-loaded safety shield to avoid visceral injury. Trocars, like Veress needles, are inserted using a sudden thrust of the pointed tip into the abdomen. Therefore, as is true with the Veress needle, placement of the trocar is also vital, and the reliance of the surgeon on mere tactile senses for proper placement can be fatal. In using the current methods, once the endoscope is in place, all other trocars used to perform the remainder of the surgical procedure are visible through the endoscope once they reach the abdominal cavity, and, therefore, their insertion is usually safe. It would be desirable, however, to also provide a visualization system in which the potential hazards associated with the insertion of the first trocar are avoided.

Endoscopes are used in a variety of surgical procedures to provide the surgeon with visual information not otherwise available. For example, the endoscope disclosed in U.S. Pat. No. 4,607,622 is used in treating, diagnosing and investigating problems with the eye. In light of its intended purposes, this endoscope provides an appropriately shaped probe which is able to receive other instruments for the purpose of treating the eye while the instrument is in the view of the endoscope. Similarly, the laser endoscope disclosed in U.S. Pat. No. 4,211,229 allows a laser instrument or other surgical device to be interchanged within the sheath of the endoscope. Disclosed in U.S. Pat. No. 3,941,121 is an endoscope through which an electrode may be inserted.

In the development of endoscopes, the provision of viewing both forward and to the side is disclosed in U.S. Pat. Nos. 3,856,000 and 3,880,148. Binocular vision, and thus improved depth perception, is provided for in the invention disclosed in U.S. Pat. No. 4,061,135 which also provides a cauterizing loop at the forward end of the endoscope. The endoscope disclosed in U.S. Pat. No. 3,941,121 may be focused to provide both microscopic and telescopic vision to the surgeon. Furthermore, the size of the endoscope in U.S. Pat. No. 3,941,121 is such that it may be inserted into a very small sheath since the device is only 18-gauge or smaller.

Many endoscopes are inserted through a sheath or tube inserted into an incision in body tissue. Thus, blindly creating an incision for the placement of a sheath can result in potential problems for many types of surgery in which an endoscope is used, not just laparoscopic surgery. It is desireable to provide an endoscope which does not require that a preliminary incision be made for placement thereof (except for an optional skin incision).

The needle endoscope disclosed in U.S. Pat. No. 3,941,121 is small enough that it may be used without a sheath and therefore avoids the need to create a preliminary incision before its insertion. However, as stated above, the insertion of this needle endoscope as well as insufflation needles and trocars ordinarily used in laparoscopic surgery require that the surgeon push the instrument into the abdomen. The force required to do so may result in the inadvertent placement of the instrument beyond the desired location and perhaps even into an organ or a major vascular structure. Thus, it is desireable to provide a method for laparoscopic surgery in which less force is required and greater control of the forward end of the instrument is achieved to thereby further reduce the risk of the procedure to the patient.

OBJECTS OF THE INVENTION

Accordingly, it is an object of the present invention to provide a method for laparoscopic surgery which reduces the amount of force required to insert a puncturing instrument and which gives the surgeon greater control over the depth to which the instrument is inserted.

It is another object of the present invention to provide a laparoscopic trocar which may be rotatably inserted into the patient.

It is another object of the present invention to provide a fiberoptic insufflation needle to be used in laparoscopic surgery which may be rotatably inserted into the patient.

It is another object of the present invention to provide a visualization system that allows the surgeon to view the insertion of the insufflation needle and all of the trocars inserted into the abdominal cavity during laparoscopic surgery.

It is still another object of the present invention to provide an endoscope which does not require that a preliminary incision be made before the placement thereof (except for an optional skin incision).

It is still another object of the present invention to provide a fiberoptic insufflation needle to be used for retroperitoneal insufflation.

SUMMARY OF THE INVENTION

The invention comprises an insufflation needle having a viewing system at its distal end, a trocar and a method for using these instruments. Both the insufflation needle and the trocar include a rotatable puncturing means and a safety shield which allow the instruments to be safely inserted into body tissue through the use of a drill thereby requiring less force and reducing the possibility of trauma to the patient. The insufflation needle also includes a viewing system which allows the surgeon to view the distal end of the needle while it is being inserted into body tissue as well as to view the distal end of the trocar once it reaches a destination within the abdominal cavity proximate the distal end of the needle. The system reduces the possibility for improper placement of both the needle and the trocar to thereby result in a safe laparoscopic surgical procedure.

DETAILED DESCRIPTION

Figure 1:
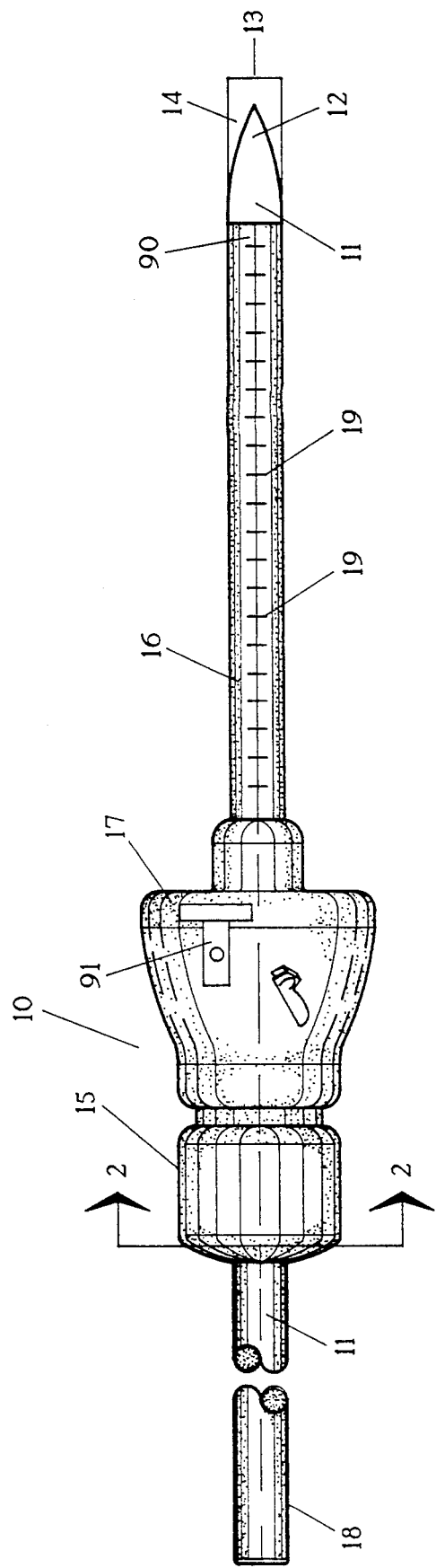
FIG. 1 shows a top view of the trocar according to the present invention.
Figure 2B:
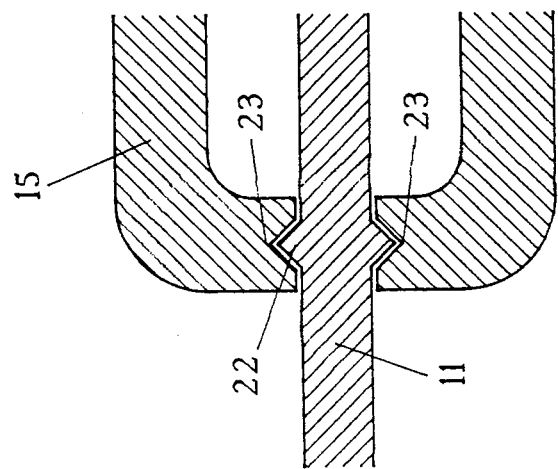
FIG. 2B shows a cross-sectional view of the trocar of FIG. 1 at line 2—2 in which the metal shaft is expanded to thereby be rotatably joined with the handle of the instrument.
Figure 2A:
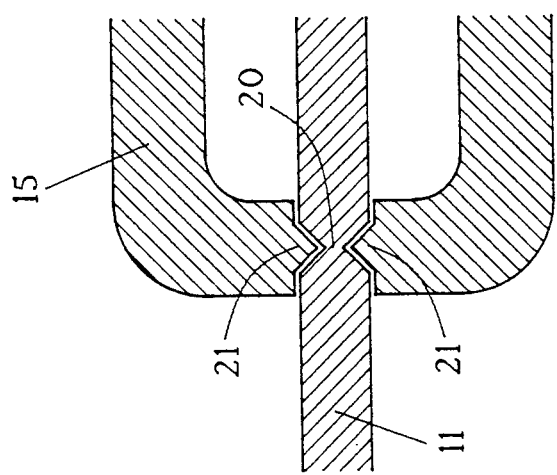
FIG. 2A shows a cross-sectional view of the trocar of FIG. 1 at line 2—2 in which the metal shaft is recessed to thereby be rotatably joined with the handle of the instrument.

Referring now to FIG. 1, there is shown a top view of the trocar according to the present invention. Trocar 10 includes metal shaft 11 which provides a means for puncturing body tissue. In this embodiment, shaft 11 has conically-shaped tip 12 at distal end 13 of trocar 10. Shaft 11 is disposed within safety shield 14, a hollow tube, which is movable between an extended position, as shown, in which safety shield 14 prevents tip 12 of shaft 11 from puncturing body tissue and a retracted position in which safety shield 14 allows tip 12 of shaft 11 to puncture body tissue. Safety shield 14 is connected to first handle portion 15 such that safety shield 14 is biased toward its extended position. The mechanisms used for connection between safety shield 14 and first handle portion 15 and for biasing of safety shield 14 are well known in the art and are illustrated by the Auto Suture(®) SurgiPort trocars manufactured by Auto Suture Company, a division of the United States Surgical Corporation of Norwalk, Conn. Shaft 11 extends from distal end 13 of trocar 10 through first handle portion 15 to operative end 18 of trocar 10. shaft 11 is rotatably connected to first handle 15 such that shaft 11 rotates with respect to the longitudinal axis of trocar 10 and with respect to first handle portion 15 and safety shield 14. FIGS. 2A and 2B show cross-sectional views of the trocar of FIG. 1 at line 2—2 illustrating the manner in which shaft 11 may be rotatably connected to first handle portion 15. In FIG. 2A, shaft 11 comprises recessed shaft portion 20 into which fits extended handle portion 21 such that shaft 11 is able to rotate with respect to first handle portion 15, to safety shield 14, and to the longitudinal axis of trocar 10. Similarly, FIG. 2B shows shaft 11 comprising expanded shaft portion 22 fitting into recessed handle portion 23 to result in the rotatable connection of shaft 11 to first handle portion 15. It will be appreciated that other mechanisms well known in the art may be used to rotatably connect shaft 11 to first handle portion 12.

In this embodiment, trocar 10 further comprises sheath 16, also known as a trocar cannula, connected to second handle portion 17. Sheath 16 forms a channel through which shaft 11 and safety shield 14 may be inserted. Second handle portion 17 may include an interior seal (not shown) which selectively prevents the passage of gas or fluid from distal end 90 of sheath 16.

Trocar 10 of this embodiment also includes horizontal depth markings 19 which are perpendicular to the longitudinal axis of trocar 10. Horizontal depth markings 19 provide the surgeon with an indication of the depth distal end 13 has been inserted into body tissue.

As is well known in the art, trocar 10 may also include a means for introducing gas or fluid into the channel of sheath 16 such as valve 91. Additionally, trocar 10 may include a threaded sheath (not shown) about sheath 16 which assists in securing trocar 10 to body tissue.

Figure 5:
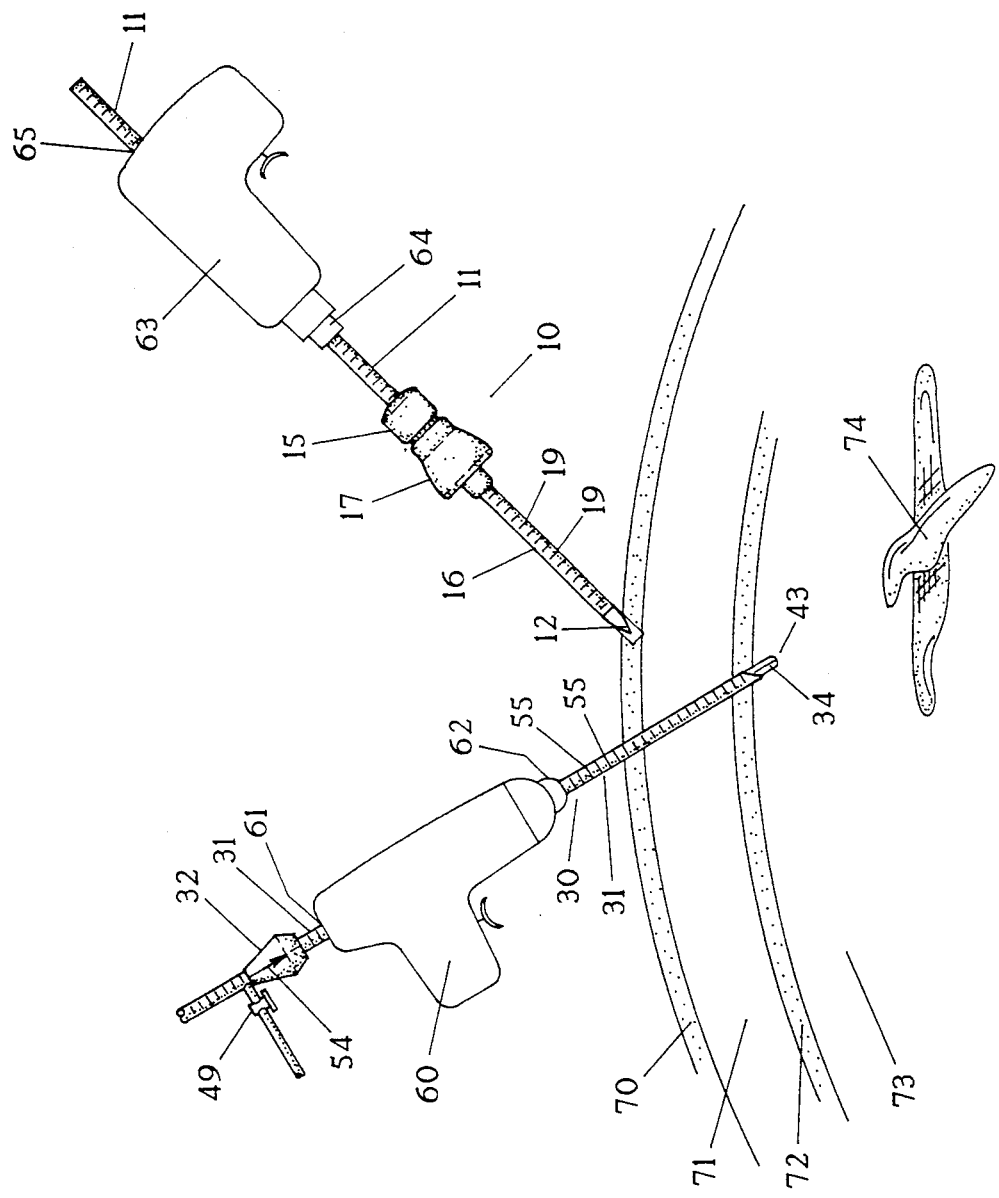
FIG. 5 shows a view of the use of the insufflation needle of FIG. 1 and the trocar of FIG. 4 during laparoscopic surgery, including the visualization of a trocar inserted into the abdominal cavity.

It will be appreciated by those of skill in the art that trocar 10 may be inserted into body tissue while rotating shaft 11. Such rotation may be accomplished through connection of shaft 11 to a motor, or drill, as is illustrated in FIG. 5 and which will be discussed in greater detail later in this description. The rotation of shaft 11 allows the surgeon to insert trocar 10 while applying less force than is normally required. As a result, the surgeon is able to exercise greater control over the depth to which trocar 10 is inserted into body tissue. Thus, trocar 10 is much safer to insert than conventional trocars which are instantaneously plunged into body tissue.

Figure 3:
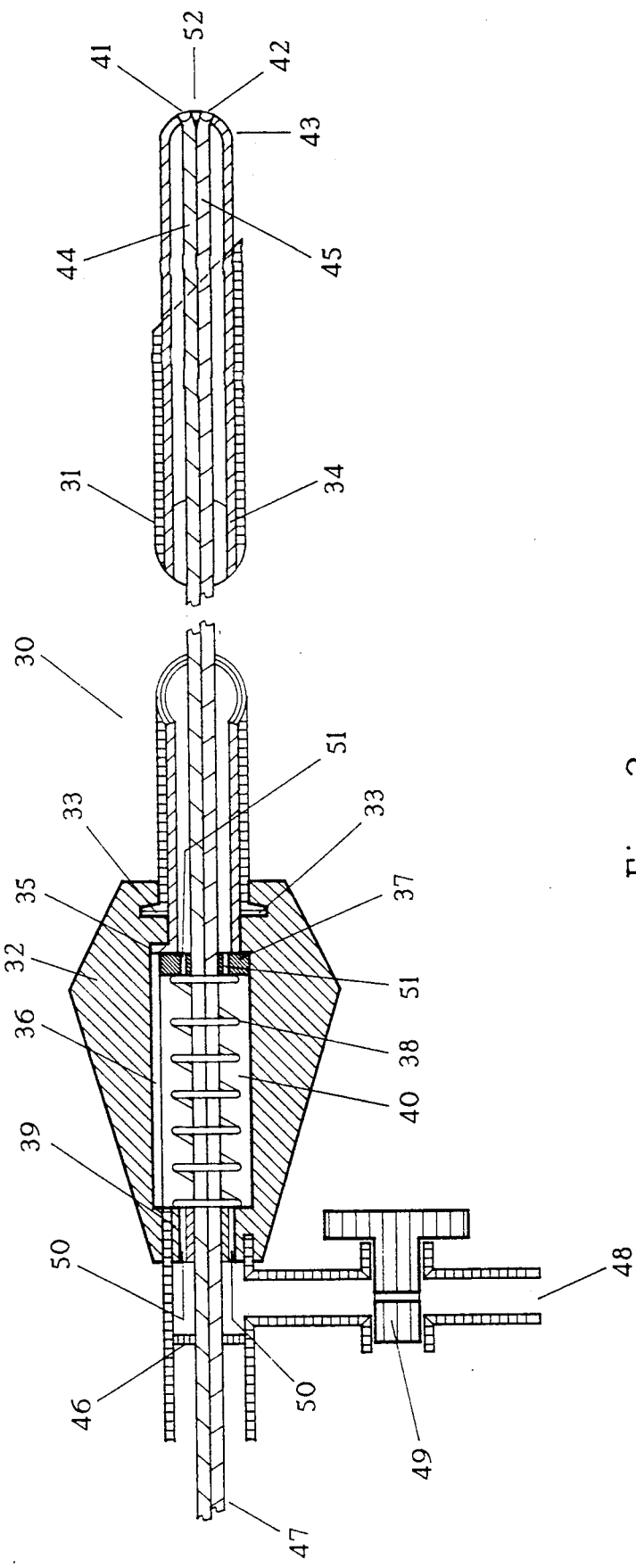
FIG. 3 shows a longitudinal cross-sectional view of one embodiment of the body of insufflation needle of the present invention.

FIG. 3 shows a longitudinal cross-sectional view of one embodiment of the body of insufflation needle of the present invention. Insufflation needle 30 includes hollow tube 31 which provides a means for puncturing body tissue. Tube 31 is connected to handle 32 such that ring 33 of tube 31 is able to rotate about the longitudinal axis of needle 30 but is not movable along the longitudinal axis of needle 30. Insufflation needle 30 also includes obturator 34 disposed within tube 31. Tab 35 of obturator 34 resides within longitudinal recess 36 of handle 32 such that obturator 34 is unable to rotate about the longitudinal axis of needle 30 and is unable to rotate with respect to handle 32. Obturator 34 is affixed to sliding ring 37 which is connected to spring bias means 38. Bias means 38 is also affixed to rearward portion 39 of handle 32. This configuration allows sliding ring 37 to move longitudinally within recess 40 of handle 32. Furthermore, obturator 34 moves between its extended position, as shown, in which obturator 34 prevents tube 31 from puncturing body tissue and its retracted position in which bias means 38 is further compressed and in which obturator 34 allows tube 31 to puncture body tissue. Without compressional forces applied at distal end 43 of needle 30, obturator 34 is biased by bias means 38 toward its extended position.

Needle 30 also includes a visualization system. Light emitting viewport 41 and light receiving viewport 42 are located at distal end 43 of needle 30. Receiving viewport 42 is positioned to provide the surgeon with a view which is substantially parallel to the longitudinal axis of needle 30. Connected to light emitting viewport 41 is emitting optic fiber 44 which is disposed within needle 30 and which extends to operative end 47 of needle 30 at its opposing end. Similarly, light receiving optic fiber 45 is disposed within needle 30 and is operatively connected to receiving viewport 42 at one of its ends and extends to operative end 47 of needle 30 at its opposing end. Specifically, in this embodiment, emitting and receiving optic fibers 44 and 45 extend from emitting and receiving viewports 41 and 42, respectively, through the longitudinal axis of obturator 34, through sliding ring 37, through recess 40 of handle 32, through rearward portion 39 of handle 32, and through seal 46 until emitting and receiving optic fibers 44 and 45 reach operative end 47 of needle 30. In passing through sliding ring 37, rearward portion 39 of handle 32 and seal 46, emitting and receiving optic fibers 44 and 45 tightly engage these surfaces so as to prevent the passage of gas or fluid therebetween. Fibers 44 and 45 are connected to a conventional visualization system (eyepiece and light source) as is well-known in the art.

In addition to providing a visualization system, needle 30 also includes a means for introducing gas of fluid into needle 30. Specifically, a gas supply is connected to supply tube 48 located at operative end 47 of needle 30. Within supply tube 48 is positioned two-way stop-cock valve 49. When valve 49 is in its open position, as shown, gas or fluid is allowed to pass through handle apertures 50 of rearward portion 39 of handle 32 and through sliding ring apertures 51 to reach the interior of obturator 34. Exit port 52 positioned at distal end 43 of needle 30 provides a means for allowing gas or fluid to flow outward from distal end 43 of needle 30.

It will be appreciated by those of skill in the art that obturator 34 includes a rotatable puncturing means, hollow tube 31. Like trocar 10 discussed above, tube 31 may be connected inserted into a drill, such as the type similar to the System II Wire Driver manufactured by Stryker, to rotate tube 31 for insertion into body tissue.

It will be further appreciated that needle 30 includes a visualization system which permits for viewing of the area near distal end 43 of needle 30 while needle 30 is being inserted into body tissue. The visualization system further contributes to a safer laparoscopic surgical procedure by providing the surgeon with visual feedback as to the position of needle 30 when distal end 43 is immersed or submerged into body tissue. Tactile sense are no longer relied upon exclusively by the surgeon as is done with conventional veress needles. Therefore, thin patients in which the fascia and peritoneum "feel" like a single layer are no longer in danger of the needle extending beyond the abdominal cavity. The same is true for patients who have previously had surgery or who have cancer for whom the intestines may be stuck to the peritoneum as such conditions will be visually detected by the surgeon. Also, the surgeon will be aware of the position of needle 30 whether or not obturator 34 has returned to its extended position. Furthermore, the location of exit port 52 proximate emitting and receiving viewports 41 and 42 assists in providing a clear view beyond distal end 43 of needle 30. This is particularly important when needle 30 is being inserted into fatty tissue. The flow of gas or fluid through exit port 52 pushes such fatty tissue away from distal end 43 such that the fatty tissue does not interfere with or obstruct the view seen through receiving viewport 42.

Figure 4A:
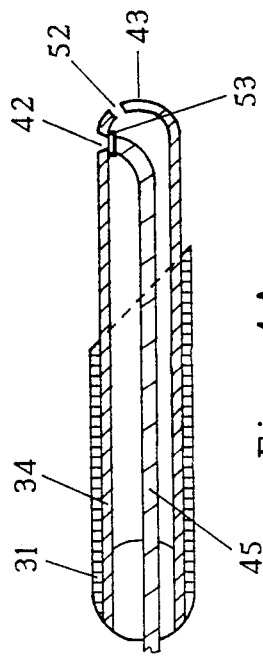
FIG. 4A shows a longitudinal cross-sectional view of the distal end of a second embodiment of the insufflation needle of the present invention in which the viewports are side-viewing.
Figure 4A:
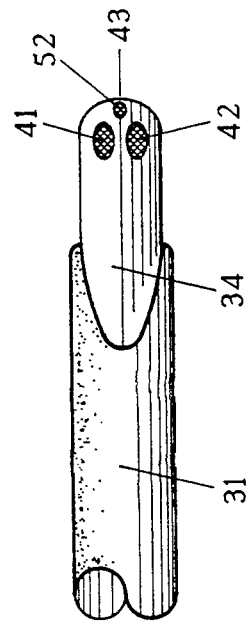

Referring now to FIG. 4A, there is shown a longitudinal cross-sectional view of the distal end of a second embodiment of the insufflation needle of the present invention in which the viewports are side-viewing. Receiving optic fiber 45 is connected to light receiving viewport 42 by bracket 53. Similarly, bracket 53 serves to connect emitting optic fiber 44 (not shown) to light emitting viewport 41 (not shown).

Figure 4B:
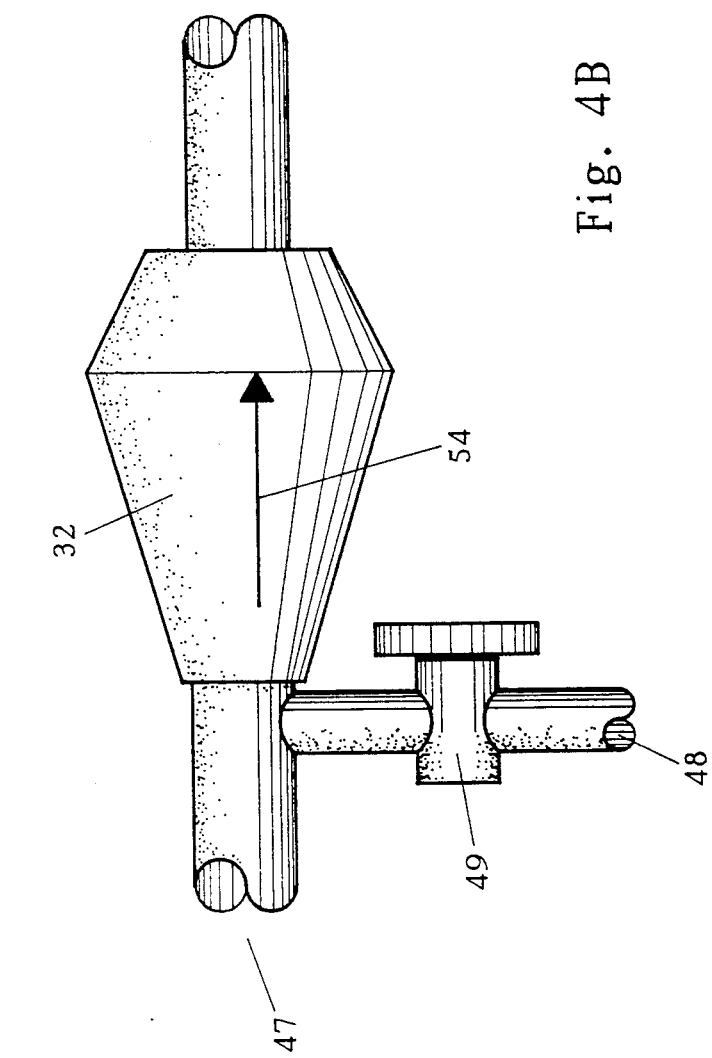
FIG. 4B shows a top view of the embodiment of the insufflation needle shown in FIG. 4A.

FIG. 4B shows a top view of the embodiment of the insufflation needle shown in FIG. 4A. As is evident in this view, receiving viewport 42 of this embodiment is positioned to provide the surgeon with a view which is substantially perpendicular to the longitudinal axis of needle 30. Furthermore, alignment mark 54 is positioned at operative end 47 of needle 30, specifically on handle 32, to provide an indication to the surgeon of the radial viewing orientation of receiving viewport 42. Mark 54 is useful to the surgeon when distal end 43 of needle 30 is immersed or submerged into body tissue.

Referring to FIG. 5, there is shown a view of the use of the insufflation needle of FIGS. 3 or 4A-B and the trocar of FIG. 1 during laparoscopic surgery, including the visualization of a trocar inserted into the abdominal cavity. Insufflation needle 30 in this illustration also includes horizontal needle markings 55 on distal end 43 of needle 30 which are perpendicular to the longitudinal axis of needle 30 and which provide the surgeon with an indication of the depth to which distal end 43 of needle 30 is inserted into body tissue. To begin the laparoscopic surgical procedure, needle 30 is inserted into drill 60. Drill 60 may be of the type similar to the System II Wire Driver manufactured by Stryker. Specifically, distal end 43 of needle 30 is inserted through rear portion 61 of drill 60 to extend through and past chuck 62. Chuck 62 is tightened to securely attach tube 31 to drill 60. In this manner, when drill 60 is engaged, tube 31 rotates with respect to the longitudinal axis of needle 30 while handle 32 and obturator 34 do not rotate. After engaging drill 60, insufflation needle 30 is positioned near the point of fascia 70 through which needle 30 is to be inserted. The surgeon then applies a small force along the longitudinal axis of tube 31 to thereby insert needle 30 through fascia 70, through preperitoneal space 71, through peritoneum 72 and into abdominal cavity 73. During insertion, the surgeon continues to rotate tube 31 while introducing gas through supply tube 48 with valve 49 in its open position and while viewing distal end 43 of needle 30 through receiving viewport 42 until distal end 43 of needle 30 reaches the desired position within abdominal cavity 73. The visualization system permits the surgeon to make certain that bowel 74 is not inadvertently punctured. If, however, bowel 74 is punctured, this will be visible permitting the surgeon to immediately withdraw needle 30 until it resides within abdominal cavity 73 thereby reducing injury to the bowel. After needle 30 is properly positioned, the surgeon may continue to allow gas or fluid to enter needle 30 to fill abdominal cavity 73. Also, chuck 62 may be loosened so that drill 60 may be repositioned closer to handle 32 so that it is further removed from the surgical site.

It will be appreciated by those of skill in the art that the gas supplied to insufflation needle 30 during the insertion of needle 30 may be controlled by the surgeon. Since the surgeon is provided with visual feedback regarding the position of distal end 43 of needle, the surgeon may choose to turn off the gas supply once inside preperitoneal cavity 71 and before puncturing peritoneum 72 to assist in keeping from pushing away the elastic peritoneum 72. Then, after puncturing peritoneum 72, gas may again be allowed to flow through needle 30 by turning valve 49 to thereby fill abdominal cavity 73.

It will also be appreciated that insufflation needle 30 may be used in surgical procedures which require retroperitoneal insufflation.

Once insufflation needle 30 is in position within abdominal cavity 73, trocar 10 may be inserted into second drill 63 through second drill chuck 64 and extending through rear portion 65 of second drill 63. Then, second drill chuck 64 is tightened to securely attach shaft 11 to second drill 63. Trocar 10 is then positioned at a point of fascia 70 near the point at which insufflation needle 30 has been inserted. If needle 30 is of the side-viewing construction, handle 32 of needle 30 may be rotated so the viewports are facing the anticipated insertion point of trocar 10. By engaging drill 63, shaft 11 rotates while all other elements of trocar 10 do not rotate. While applying a small force along longitudinal axis of shaft 11, the surgeon views abdominal cavity 73 through receiving viewport 42 on insufflation needle 30 until tip 12 reaches the desired position proximate distal end 43 of insufflation needle 30 within abdominal cavity 73 and is visible through receiving viewport 42 of needle 30. Once trocar 10 is in the proper position, the surgeon may loosen second drill chuck 64 so that drill 63 may be slid toward operative end 18 of trocar 10 and removed from shaft 11.

It will be appreciated by those with skill in the art the insertion of a trocar by this method does not require a great deal of force and allows the surgeon to view the area into which the trocar is being inserted. Thus, the possibilities of injury or trauma to the patient are significantly reduced over conventional methods whereby the trocar is blindly and suddenly thrust into body tissue. The possibilities that such an instrument is inserted so its tip resides within the preperitoneal space or beyond the abdominal cavity into an organ or a vascular structure is also reduced. When used with the visualization system of needle 30, the surgeon no longer relies exclusively on tactile senses for proper placement of trocar 10. Furthermore, the surgeon will be aware of the fact that the trocar is in position, regardless of whether or not safety shield 14 has returned to its extended position.

It will be further appreciated that trocar 10 need not necessarily be used in conjunction with insufflation needle 30. If, for example, multiple trocars are required for the completion of laparoscopic surgery, trocar 10 may be used for this purpose.

It will also be appreciated that needle markings 55 along tube 31 of insufflation needle 30 and trocar markings 19 along sheath 16 which are perpendicular to their longitudinal axes further assist the surgeon in determining the approximate depths of body tissue through which needle 30 and trocar 10 are inserted. By first inserting insufflation needle 30, the surgeon may note the extent to which distal end 43 of insufflation needle 30 is inserted. The noted value of depth then serves as a guide for the depth to which trocar 10 is to be inserted into body tissue proximate needle 30 thereby allowing the surgeon to be cognizant of the depth of trocar 10 during its insertion and providing a safety precaution that may be used in conjunction with the visualization system of needle 30.

It will be further appreciated that, once inserted, shaft 11 and safety shield 14 of trocar 10 may be withdrawn from sheath 16 and second handle portion 17. Sheath 16 and second handle portion 17 remain in place and serve as a port through which another laparoscopic device, such as an endoscope with a wider field of view, may be inserted. The seal within second handle portion 17 prevents the flow of gas or fluid from within abdominal cavity 73 from unintentionally escaping therefrom.

Figure 6:
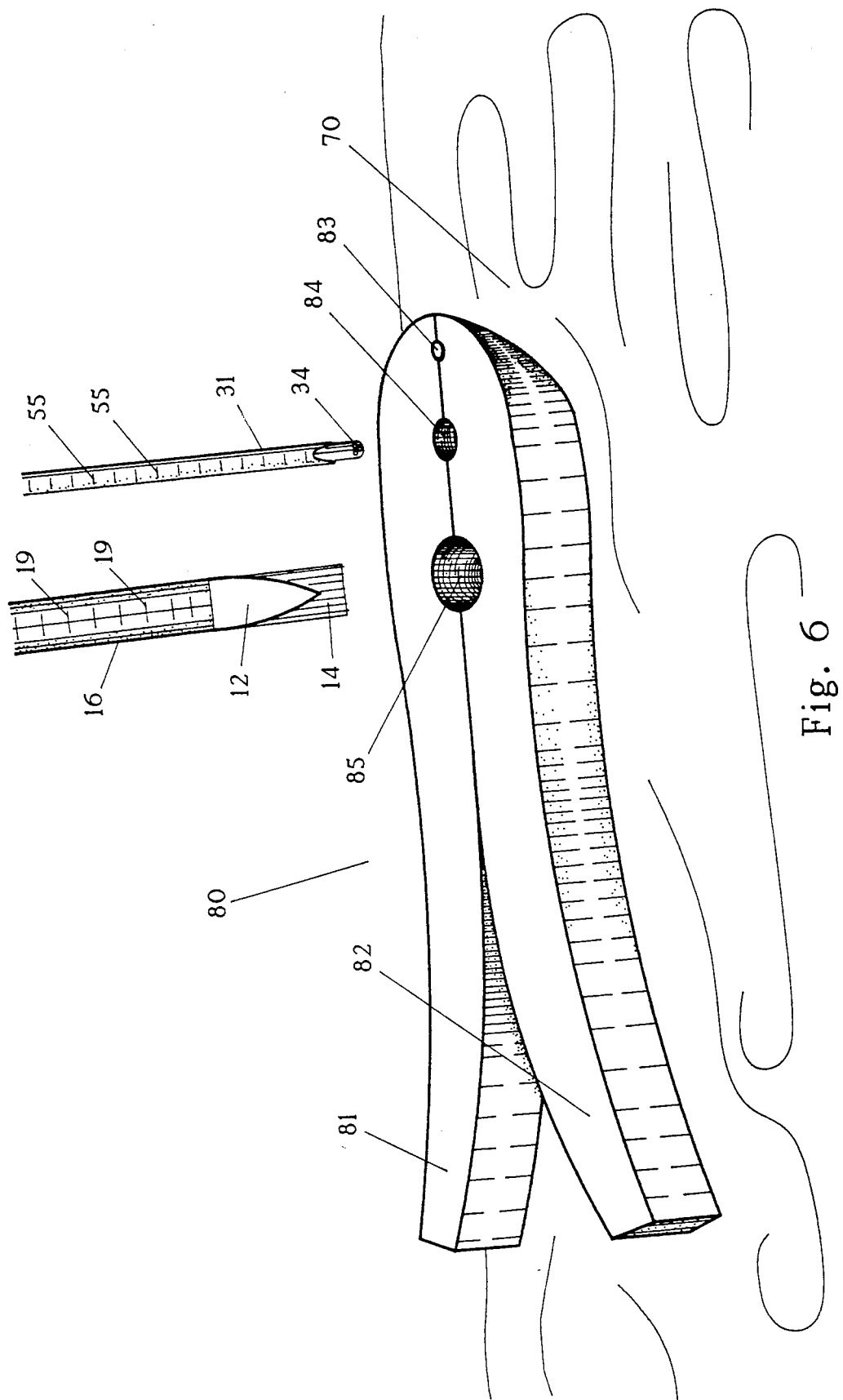
FIG. 6 shows a perspective view of the guide bracket of the present invention.

FIG. 6 shows a perspective view of the guide bracket of the present invention that may be used to assist the surgeon in positioning needle 30 and trocar 10 of the present invention. Guide bracket 80 is comprised of first and second opposing handles 81 and 82 rotatably connected by pivot fastener 83. When guide bracket 80 is in its closed position, as shown, the engaging surfaces of first and second handles 81 and 82 form first and second apertures 84 and 85. First aperture 84 is of a diameter slightly larger than the diameter of tube 31 of needle 30 and second aperture 85 is of a diameter slightly larger than sheath 16 of trocar 10. Also, first and second apertures 84 and 85 are formed such that when needle 30 and trocar 10, respectively, are inserted into first and second apertures 84 and 85, they will enter fascia 70 of the patient at an angle which is substantially perpendicular to fascia 70. The first and second apertures 84 and 85 are separated by approximately 0.5 centimeters.

To use guide bracket 80, the surgeon places guide bracket 80 on the patient's abdomen in its closed position, as shown. The surgeon then inserts needle 30 through first aperture 84 until distal end 42 of needle 30 reaches the patients abdominal cavity as illustrated in FIG. 5. If the embodiment of needle 30 shown in FIGS. 4A and 4B having a side viewing receiving port is used, needle 30 is rotated by the surgeon until alignment mark 54 (see FIG. 4B) is facing second aperture 85 so that the surgeon is certain that needle 30 is properly aligned to view distal end 13 of trocar 10 when it reaches the patient's abdominal cavity. Next, the surgeon inserts trocar 10 through second aperture 85 according to the method discussed above until distal end 13 of trocar 10 is visible through the receiving viewport of needle 30.

I claim:

1. A laparoscopic insufflation needle having a longitudinal axis, a distal end an operative end, comprising:
   a rotatable body tissue puncturing means, the puncturing means having a distal end, an operative end and a longitudinal axis, such that the puncturing means rotates about its longitudinal axis, the puncturing means being adapted to be rotated by a motor;
   a safety shield movable between an extended position in which the shield prevents the puncturing means from puncturing body tissue and a retracted position in which the shield allows the puncturing means to puncture body tissue, and the safety shield being biased toward its extended position;
   a light emitting viewport positioned within the puncturing means and positioned at the distal end of the needle;
   a light receiving viewport positioned within the puncturing means and positioned at the distal end of the needle;
   a light emitting optic fiber having opposing ends, disposed within the needle, and operatively connected to the emitting viewport at one of its ends and extending to the operative end of the needle at its opposing end;
   a receiving optic fiber having opposing ends, disposed within the needle, and operatively connected to the receiving viewport at one of its ends and extending to the operative end of the needle at its opposing end;
   a means for introducing gas or fluid into the needle; and
   a means for allowing gas or fluid to flow outward from the distal end of the needle.

2. The laparoscopic insufflation of claim 1 wherein the receiving viewport is positioned to provide a view parallel with the longitudinal axis of the insufflation.

3. The laparoscopic insufflation needle of claim 1 wherein the receiving viewport is positioned to provide a view substantially perpendicular to the longitudinal axis of the insufflation needle.

4. The laparoscopic insufflation needle of claim 3 further comprising a mark on the operative end of the insufflation needle indicating the radial orientation of the receiving viewport.

5. The laparoscopic insufflation needle of claim 1 wherein the puncturing means comprises a hollow tube and the safety shield comprises an obturator positioned within the puncturing means.

6. The laparoscopic insufflation of claim 1 further comprising horizontal markings on the distal end of the puncturing means perpendicular to the longitudinal axis of the insufflation needle which provide an indication of the depth the distal end of the insufflation needle is inserted into body tissue.

7. A method of laparoscopic surgery, comprising the steps of:
   providing the insufflation needle of claim 1;
   providing a first motor;
   connecting the first motor to the insufflation needle;
   positioning the distal end of the insufflation needle near body tissue into which the insufflation needle is to be inserted;
   rotating the puncturing means by engaging the first motor;
   introducing gas or fluid pressure into the needle;
   applying force along the longitudinal axis of the puncturing means to thereby insert the insufflation needle into body tissue while
   continuing to rotate the puncturing means,
   controlling the introduction of gas of fluid pressure into the needle, and
   viewing the position of the distal end of the surgical instrument through the receiving optic fiber until the distal end of the surgical instrument reaches the desired position.

8. The method of claim 7, further comprising the steps of:
   providing a laparoscopic surgical instrument having a longitudinal axis, a distal end and an operative end, the instrument comprising:
   a handle;
   a rotatable body tissue puncturing means rotatably connected to the handle,
      the puncturing means having a distal end, an operative end and a longitudinal axis, such that the handle is disposed between the operative and distal ends of the puncturing means, and such that the puncturing means rotates about its longitudinal axis, and the puncturing means being adapted to be rotated by a motor; and
   a safety shield operatively connected to the handle and movable between an extended position in which the shield prevents the puncturing means from puncturing body tissue and a retracted position in which the shield allows the puncturing means to puncture body tissue, and the safety shield being biased toward its extended position;
   providing a second motor;
   connecting the second motor to the surgical instrument;
   positioning the distal end of the surgical instrument near body tissue into which the surgical instrument is to be inserted and near the point at which the insufflation needle is inserted into body tissue such that the light receiving viewport of the insufflation needle is oriented toward the surgical instrument;
   rotating the puncturing means of the surgical instrument by engaging the second motor;
   applying force along the longitudinal axis of the puncturing means of the surgical instrument to thereby insert the surgical instrument into body tissue while continuing to rotate the puncturing means of the surgical instrument and while viewing the position of the distal end of the surgical instrument through the receiving optic fiber of the insufflation needle until the distal end of the surgical instrument reaches the desired position.

* * * * *